(12) United States Patent
Kaiser et al.

(10) Patent No.: US 10,136,863 B2
(45) Date of Patent: Nov. 27, 2018

(54) X-RAY-OPTIMIZED DEVICE FOR SUPPORTING A PATIENT

(71) Applicant: MAQUET GMBH, Rastatt (DE)

(72) Inventors: Jochen Kaiser, Karlsruhe (DE); Ulrich Wyslucha, Weingarten (DE); Siegfried Hund, Oberkirch (DE)

(73) Assignee: MAQUET GMBH, Rastatt (DE)

( * ) Notice: Subject to any disclaimer, the term of this patent is extended or adjusted under 35 U.S.C. 154(b) by 127 days.

(21) Appl. No.: 15/130,095

(22) Filed: Apr. 15, 2016

(65) Prior Publication Data

US 2016/0242708 A1 Aug. 25, 2016

Related U.S. Application Data

(63) Continuation-in-part of application No. PCT/EP2014/072323, filed on Oct. 17, 2014.

(30) Foreign Application Priority Data

Oct. 18, 2013 (DE) ........................ 10 2013 111 523

(51) Int. Cl.
*A61B 6/04* (2006.01)
*A61G 13/10* (2006.01)
*A61G 13/12* (2006.01)

(52) U.S. Cl.
CPC .......... *A61B 6/0407* (2013.01); *A61G 13/101* (2013.01); *A61G 13/122* (2013.01); *A61G 13/123* (2013.01); *A61G 2210/50* (2013.01)

(58) Field of Classification Search
CPC ...................................................... A61B 6/04
(Continued)

(56) References Cited

U.S. PATENT DOCUMENTS 3,766,384 A 10/1973 Anderson
5,088,706 A * 2/1992 Jackson ................. A61G 13/00
5/608

(Continued)

FOREIGN PATENT DOCUMENTS

CN 2102687 U 4/1992
CN 202124846 U 1/2012
(Continued)

OTHER PUBLICATIONS

Translated Second Office Action for CN201480057124.1, which corresponds to this application, dated Aug. 3, 2017, 25 pages (Search report found on pp. 9-10).

(Continued)

*Primary Examiner* — Frederick C Conley
(74) *Attorney, Agent, or Firm* — Aaron M. Miller

(57) ABSTRACT

An apparatus for supporting a patient is disclosed. The apparatus includes a first structural member having a first end portion and a second end portion, the second end portion of the first structural member being attached to an operating table. The apparatus also includes a second structural member having a first end portion and a second end portion, the second end portion of the second structural member being attached to the operating table. The apparatus further includes a first connecting member that connects the first end of the first structural member to the first end of the second structural member, the first structural member being disposed at a predetermined distance from the second structural member. The apparatus also includes a first support member supported on the first structural member, the first support member configured to support a body part of the patient.

20 Claims, 2 Drawing Sheets

(58) Field of Classification Search
USPC .............................................. 5/613, 621–624
See application file for complete search history.

(56) References Cited

U.S. PATENT DOCUMENTS

| | | | |
|---|---|---|---|
| 5,131,106 | A | 7/1992 | Jackson |
| 5,147,287 | A | 9/1992 | Jewell et al. |
| 5,806,117 | A | 9/1998 | Gotfried |
| 6,076,525 | A | 6/2000 | Hoffman |
| 6,154,901 | A | 12/2000 | Carr |
| 7,520,007 | B2 | 4/2009 | Skripps |
| 7,600,281 | B2 | 10/2009 | Skripps |
| 2005/0081865 | A1 | 4/2005 | Hubert et al. |
| 2006/0248650 | A1* | 11/2006 | Skripps .................. A61G 13/04 5/621 |
| 2006/0255220 | A1 | 11/2006 | Skripps |
| 2006/0284468 | A1 | 12/2006 | Tanaka |
| 2013/0269710 | A1 | 10/2013 | Hight et al. |

FOREIGN PATENT DOCUMENTS

| | | |
|---|---|---|
| CN | 202933180 U | 5/2013 |
| DE | 102006059733 A1 | 6/2008 |
| DE | 102009004554 A1 | 7/2009 |
| DE | 202013100213 U1 | 3/2013 |
| EP | 1785123 A2 | 5/2007 |
| EP | 2325502 A1 | 5/2011 |
| RU | 2161942 C1 | 1/2001 |
| WO | 2009/029524 A1 | 3/2009 |
| WO | 2013/069952 A1 | 5/2013 |
| WO | 2014/057344 A2 | 4/2014 |

OTHER PUBLICATIONS

International Search Report dated Feb. 23, 2015 issued for corresponding international application No. PCT/EP2014/072323, 3 pages, with translation (2 pages).
Chinese Office Action and Chinese Search Report (Chinese and English translations) dated Jan. 25, 2017 which issued during the prosecution of corresponding Chinese patent application No. 201480057124.1, 23 pages.
Russian Office Action and Search Report (with English translations) dated Mar. 27, 2018, which issued for corresponding Russian Patent Application No. 2016118973, 11 pages.

* cited by examiner

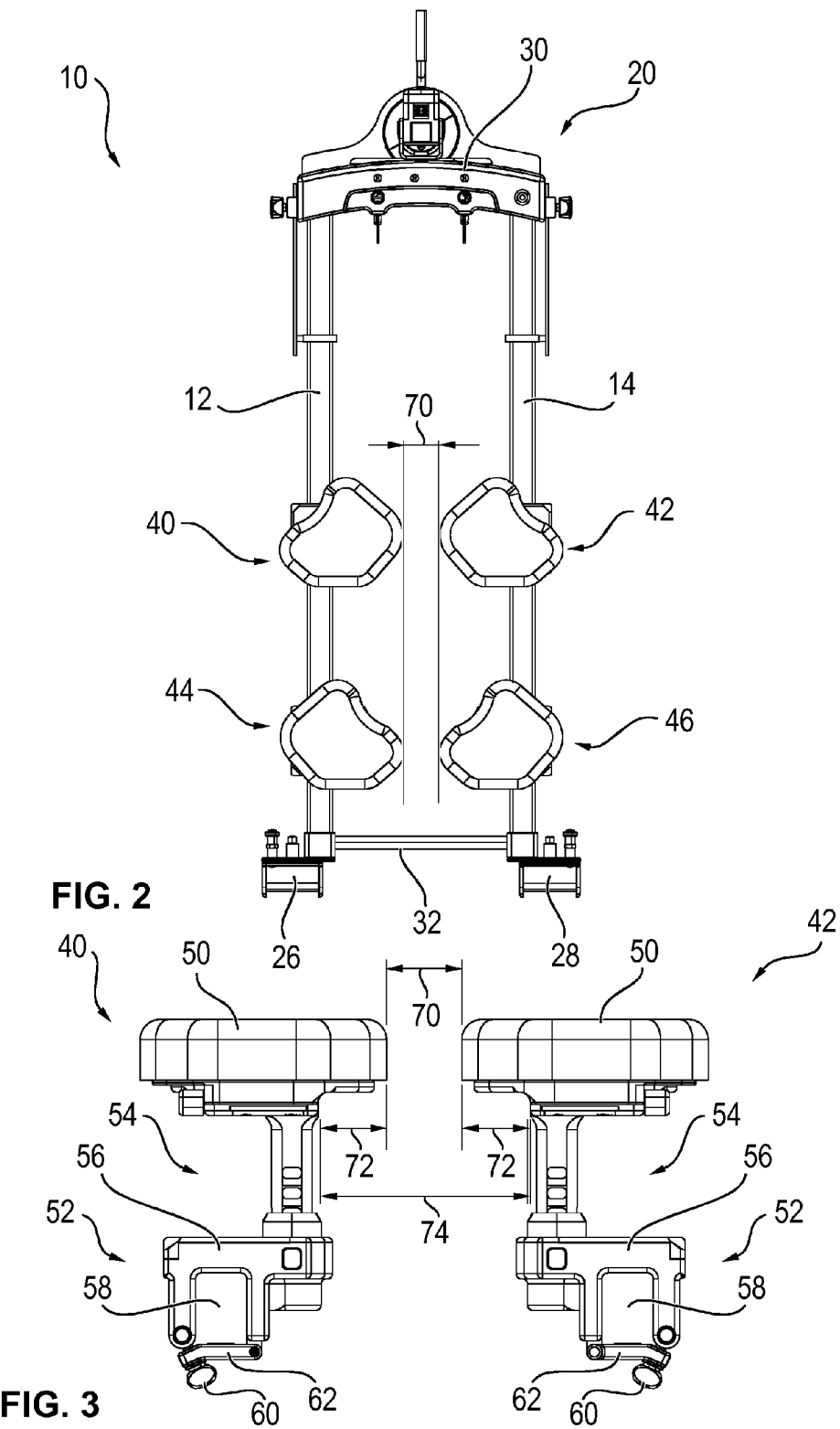

X-RAY-OPTIMIZED DEVICE FOR SUPPORTING A PATIENT

CROSS REFERENCE TO RELATED APPLICATIONS

The present application a continuation-in-part filed under 35 U.S.C. § 111(a), and claims the benefit under 35 U.S.C. §§ 365(c) and 371 of PCT International Application No. PCT/EP2014/072323, filed Oct. 17, 2014, and which designates the United States of America, and German Patent Application No. 10 2013 111 523.3, filed Oct. 18, 2013. The disclosures of these applications are herein incorporated by reference in their entirety.

TECHNICAL FIELD

The present disclosure relates to an apparatus for supporting a patient, which may comprise a first rail, which can be fastened to an operating table, a second rail, which can be fastened to the operating table, and a connecting unit, which may connect the first end of the first rail, remote from the operating table, to the first end of the second rail, remote from the operating table, such that the two rails may be arranged at a predefined distance from one another. The apparatus may further comprise a first patient supporting unit for supporting the patient, arranged on the first rail, and a second patient supporting unit for supporting the patient, arranged on the second rail.

BACKGROUND

During some surgical operations, for example during surgeries on the spinal column, a patient may be x-rayed during surgery. For this purpose, C-arm x-ray units are typically used, in which the patient is supported within the opening of the "C". C-arms that are pivotable up to 270° are also used for recording 3-D images. Traditional operating tables typically are not used or are used in a limited manner for supporting the patient, because such tables may not permit suitable x-raying. To record 3-D images, the C-arm is moved relatively closely to the patient over a relatively large range. Standard patient supports on operating tables may be too wide to be suitable for this purpose. Moreover, such operating tables may comprise relatively thick structures that contain metal, resulting in x-rays of insufficient quality. The thickness and contours of the structures may vary widely, which may result in unsuitable quality of the x-ray image, and may result in unsuitable radiographic exposure via the C-arm.

For these reasons, apparatuses for supporting a patient may be used which can be fastened to the operating table. In such cases, the patient rests with his upper body, where the surgery will be performed and which is x-rayed, on the attached apparatus and with his legs on the actual operating table.

An apparatus of this type for supporting a patient during surgery is known, for example, from U.S. Pat. No. 7,600,281 B2. The apparatus described therein comprises two side rails, extending parallel to one another and connected at one end to the operating table and at the other end to a support assembly. On the side rails a plurality of supporting surfaces are provided, on which the patient can be supported, particularly at the upper body and hips. These supporting surfaces project over the area between the two side rails.

The above-described apparatus has the disadvantage that the supporting elements may cause the recorded x-ray image to be unsuitable. In addition, the recording of 3-D images may be difficult because the components may present an obstacle to movement of the C-arm. The contours of the supporting elements may show up in the x-ray image, which can result in unsuitable x-ray images. Furthermore, the rigid supporting elements may result in unsuitable adjustment to the individual anatomy of the patient. Therefore, the patient may not be suitably supported during surgery.

SUMMARY OF THE DISCLOSURE

An apparatus for supporting a patient that may provide suitable support of the patient while at the same time providing suitable x-ray images to be recorded, including for example 3-D images, is disclosed.

In at least some exemplary embodiments, the first patient supporting unit may be mounted (e.g., exclusively mounted on or exclusively supported by) on the first rail and the second patient supporting unit may be mounted (e.g., exclusively mounted on or exclusively supported by) on the second rail. The first and second patient supporting units may be mounted and configured such that, even when the patient supporting units are arranged opposite one another (e.g., disposed spaced apart from one another), an x-ray area that is free of material may be formed between the two patient supporting units. For example, because there may be no material that will absorb or reflect x-rays within the x-ray area, a substantially complete x-ray examination of a patient supported on the patient supporting units may be performed. Thus a substantially completely undistorted x-ray image of the patient, including in 3-D, may be provided, for example at least in the material-free area (also referred to, for example, as the x-ray area). A relatively slim configuration that allows suitable movement of the C-arm may be provided. Furthermore, the distance between the patient supporting units may allow the abdomen of the patient to be unsupported, resulting in improved support of, e.g., heavyset patients.

A material-free area may include the two patient supporting units being arranged at a predetermined distance from one another, creating a space between the patient supporting units in which substantially no component is located.

The arrangement opposite one another may include two patient supporting units being arranged equidistant from the first connecting unit.

In at least some exemplary embodiments, there may be no connection between the first and second patient supporting units (e.g., no element that connects the first or the second patient supporting unit may be provided). For example, a material-free x-ray area may be provided. Also for example, the two patient supporting units can be moved independently of one another (e.g., displaced along the rails).

In at least some exemplary embodiments, the material-free x-ray area may be formed when the two patient supporting units are arranged side by side in parallel (e.g., when the two patient supporting units may be arranged on the rails equidistant from the first connecting unit).

The second end of the first rail, opposite the first end of the first rail, and the second end of the second rail, opposite the first end of the second rail, may be connected to one another via a second connecting unit. For example, the two rails may be at a predetermined distance from one another, so that to use the intended patient supporting units, for example, the sizes of these patient supporting units may be adjusted in accordance with this distance so as to produce an open space of sufficient size (for example, a material-free x-ray area of sufficient size) between the patient supporting units. The rails may be made for example of an x-rayable material, for example CFR. For example, when the C-arm is moved transversely during the recording of 3-D images, x-rays can pass through the rails, and a relatively small amount of material may be located within the beam path.

The second connecting unit may be, for example, a bar, which may be attached to the second ends of the rails and may hold these ends spaced from one another.

The first and second rails may be for example arranged parallel to one another, so that they are spaced the same distance from one another along their length (e.g., along their substantially entire length). The patient supporting units mounted on the rails may (e.g., each) have the same distance from the (e.g., respectively) other rail, irrespective of where said supporting units are positioned on the rails. Accordingly, an x-ray area of sufficient size may be provided.

In at least some exemplary embodiments, the first rail and the second rail may be connected to one another (e.g., solely) via the first connecting unit and the second connecting unit. Accordingly, a relatively large material-free area for x-raying may be provided because, irrespective of where on the rails the patient supporting units are arranged and therefore the patient may be supported, an open space may be created between the patient supporting units (e.g., in which substantially no connecting elements may be disposed between the rails and obstruct the transmission of x-rays).

In at least some exemplary embodiments, the first connecting unit may be part of a support assembly, by which for example one end of each of the rails can be supported on the floor. This support assembly may be vertically adjustable, so that the height of the rails in relation to the floor can be altered and/or adjusted to the height of the operating table. The height can also be adjusted, for example, to increase the ergonomic comfort of the surgeons.

In at least some exemplary embodiments, the other ends of the rails may be fastened to the operating table, which may be vertically adjustable, so that, together with the vertically adjustable support assembly, the rails can be adjusted so as to remain horizontally aligned.

In at least some exemplary embodiments, a first fastening unit for fastening the apparatus to the operating table may be arranged at the second end of the first rail, e.g. opposite the first end, and a second fastening unit for fastening the apparatus to the operating table may be arranged at the second end of the second rail, e.g. opposite the first end. These fastening units may be configured such that the rails can be fastened securely and reversibly to the operating table in a relatively simple manner, and such that unsuitable (e.g., unintended) detachment from the table may be substantially prevented.

In at least some exemplary embodiments, a third patient supporting unit for supporting the patient may be provided on the first rail and/or for a fourth patient supporting unit for supporting the patient may be provided on the second rail. The third patient supporting unit may be mounted (e.g., exclusively mounted on or exclusively supported by) on the first rail and the fourth patient supporting unit may be mounted (e.g., exclusively mounted on or exclusively supported by) on the second rail. These patient supporting units may be configured such that, irrespective of the arrangement thereof on the rails, a substantially material-free x-ray area may be formed.

For example, the first patient supporting unit and/or the third patient supporting unit may be displaceable independently of one another along the first rail in the longitudinal direction of the first rail. The second patient supporting unit and the fourth patient supporting unit may be mounted so as to be displaceable independently of one another along the second rail, in the longitudinal direction of the second rail. Also for example, the first and second patient supporting units and the third and fourth patient supporting units can also be displaced independently of one another (e.g., because there are no connecting elements between them). For example, this configuration may allow the arrangement of the four patient supporting units to be adjusted suitably to the individual anatomy of a patient. For example, the patient supporting units arranged side by side on the two rails may not be arranged parallel (e.g., precisely parallel) with one another, and may instead be arranged offset (e.g., slightly offset).

In at least some exemplary embodiments, the first patient supporting unit and the second patient supporting unit may support the upper body of the patient, while the third and fourth patient supporting units may support the hips of the patient. For example, the individual displaceability of the four patient supporting units may allow the two patient supporting units that serve to support the hips, for example, to be arranged at different distances from the operating table. The same may apply to the patient supporting units provided for supporting the upper body.

In at least some exemplary embodiments, the first, second, third and/or fourth patient supporting unit may be mountable on the respective rail via a quick-release fastening device that can be released and refastened. For example, the units may be easily mounted prior to surgery, or easily removed after surgery. For example, the patient supporting units can be mounted after the rails have been fastened, because the supporting units can be mounted on the rail in a radial direction by the quick-release fastening devices (e.g., they are not slid onto the rails axially). For example, the quick-release fastening device may be designed such that a mounting unit for the patient supporting unit comprises a U-shaped base, which may be placed onto the rectangular rails from the top. At the end of one of the two arms of the U-shaped base, a locking clamp may be pivotably arranged, and can be tightened by a threaded bolt on the end of the other arm of the U-shaped base, e.g. using a threaded bolt or nut that can be manually activated (e.g., without additional supplemental devices) so that a closed contour may be formed. For example, the patient supporting units may be securely mounted on the rails and may substantially prevent unsuitable (e.g., unintentional) release from occurring during the surgical operation. In the U-shaped base, anti-slip pads may be provided, which may substantially prevent the patient supporting unit from shifting on the rail when the locking clamp is closed.

In at least some exemplary embodiments, the first, second, third or fourth patient supporting unit may (e.g., each) comprise a mounting unit for mounting on the rail, a support pad on which a cushion can be positioned (e.g., on which the patient rests), and/or a height adjustment unit. The height adjustment unit may be disposed (e.g., situated) between the mounting unit and the support pad and may allow for the distance between the support pad and the mounting units to be adjusted. Thus the distance between the support pad and the rail may be adjusted, allowing the patient support to be adjusted in a substantially vertical direction to conform to the individual anatomy of the patient. The combination of the independent displacement of the patient supporting units along the rails and the vertical adjustability of the support pads may provide for a suitable adjustment for each patient.

In at least some exemplary embodiments, the support pads may be connected (e.g., fixedly connected) to the height adjustment unit and can be displaced transversely to the rail in the direction of the other rails, allowing the distance between the support pads of adjacent patient supporting units to be adjusted. The support pads may comprise for example a supporting structure mounted on the height adjustment unit and a cushion arranged on said supporting structure.

For example, the support pads of the patient supporting units may be made of a material that is radiolucent (e.g., providing for a suitable x-ray image to be produced). In addition, the support pads may be formed as having a homogeneous contour, for example a uniform thickness and material strength. For example, this homogeneity and the use of radiolucent material may allow the material-free x-ray area to be enlarged by a supplemental x-ray area (e.g., bordering thereon). This supplemental x-ray area (e.g., the area in which the patient rests on the support pad, which for example may not include the area of the rails or the height adjustment unit) may allow a suitable x-ray image to be produced (e.g., as is possible with the material-free x-ray area between the support pads). For example, the configuration of the support pads may provide for a suitable x-ray image to be produced. Thus the area (e.g., substantially nearly the entire area between the two rails) can be used to produce a suitable x-ray image. The material-free x-ray area and the supplemental x-ray area may, for example, together form an expanded x-ray area.

In at least some exemplary embodiments, the support pads may be made of a plastic (e.g., so that suitable x-ray permeability is achieved). For example, the support pads may be made of a high strength plastic such as a carbon fiber-reinforced plastic that allows the support pads to be relatively thin (e.g., so that their impact on the x-rays is minimized).

In at least some exemplary embodiments, the first rail, the second rail, the first patient supporting unit, the second patient supporting unit, the third patient supporting unit and/or the fourth patient supporting unit may be configured to be substantially free (e.g., substantially completely free) of metal. For example, if an x-ray image is recorded outside of the expanded x-ray area, the x-ray may have suitable quality. The aforementioned units may for example be made of a carbon fiber-reinforced plastic or any other suitable x-ray permeable material. This may provide for suitable x-ray images to be produced in the recording of 3-D images (e.g., when the components, for example the rails, are included in the x-ray).

In at least some exemplary embodiments, the width of the mounting units of the patient supporting units and the width of the height adjustment units of the patient supporting units may each correspond approximately to the width of the respective rail (e.g., or may be slightly wider) so that a relatively large expanded x-ray area may be formed, which may comprise the area (e.g., substantially nearly the entire area) between the two rails.

In at least some exemplary embodiments, the first rail and the second rail may be similar (e.g., substantially identical) in configuration, so that one type (e.g., a single type) of rail is produced. For example, the first, the second, the third and/or the fourth patient supporting unit may be similar (e.g., substantially identical) in configuration. Alternatively, the mounting units and the height adjustment units may be similar (e.g., substantially identical), and the support pads may be adapted to select regions of the body.

In at least some exemplary embodiments, an assembly may comprise an operating table and an apparatus for supporting a patient (e.g., as described above). The apparatus for supporting the patient may be fastened to the operating table.

In at least some exemplary embodiments, an assembly comprising an operating table, an apparatus for supporting a patient (e.g., as described above) fastened to the operating table, and/or an x-ray unit for x-raying a patient supported on the apparatus for supporting a patient may be provided.

BRIEF DESCRIPTION OF THE DRAWINGS

Additional features and advantages of the present disclosure are found in the following description, with reference to the attached set of drawings. The drawings illustrate:

FIG. 2 a plan view of an exemplary apparatus according to FIG. 1; and

FIG. 3 a side elevation of two exemplary patient supporting units of the apparatus according to FIGS. 1 and 2.

DETAILED DESCRIPTION AND INDUSTRIAL APPLICABILITY

Figure 1:
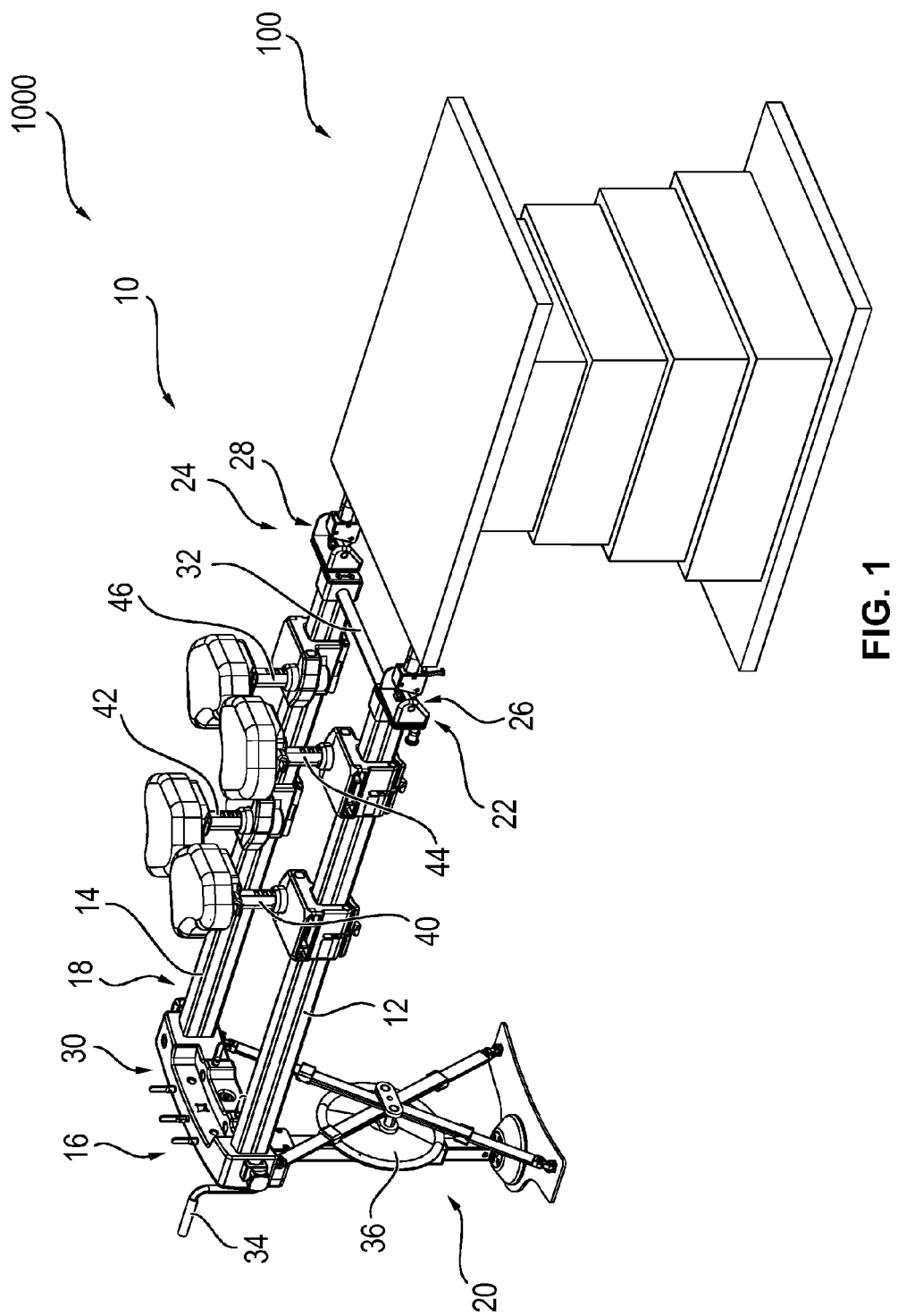
FIG. 1 a schematic, perspective representation of an exemplary assembly for supporting a patient to be x-rayed during a surgical operation.

FIG. 1 is a schematic, perspective illustration of an assembly 1000 for supporting a patient during a surgical operation. The assembly may comprise an operating table 100 and an apparatus 10 for supporting the region of the body or a body part of the patient that will be x-rayed. FIG. 2 illustrates a plan view of this apparatus 10 according to FIG. 1.

Apparatus 10 may be used, for example, for supporting patients during surgery (e.g., back surgery). During such surgeries (e.g., back surgeries), for example on the spinal column, patients may be x-rayed during surgery, for which purpose a C-shaped x-ray unit may be used. For example, the C-arm of the x-ray unit may be moved around the patient to record 3-D images. For example, apparatus 10 may be configured such that it can be used to produce a suitable x-ray image in a relatively simple manner. A patient may not be supported on a conventional operating table, because such an operating table may not allow x-rays of suitable quality of the desired areas to be produced. The solid pedestal of a conventional operating table may limit suitable x-ray length, and a conventional operating table may comprise an excess of metal-containing structural elements that may produce x-ray images of unsuitable quality. Also for example, the patient supporting surface of a conventional operating table may be relatively too wide for recording 3-D images using a pivotable C-arm.

Apparatus 10 may comprise two structural members such as, for example, rails 12, 14, the first end portions (e.g., first ends) 16, 18 of which may be mounted on a support assembly 20. The second end portions (e.g., second ends) 22, 24 of rails 12, 14, which may be opposite of first ends 16, 18, can be fastened via fastening assemblies such as fastening units 26, 28 to operating table 100, for example at interfaces for connecting operating table 100 to leg panels.

Support assembly 20 may serve to support rails 12, 14 on the floor and also to ensure that a predetermined distance may be maintained between rails 12, 14. For example, support assembly 20 may comprise a connecting member such as a connecting unit 30, via which the two first ends 16, 18 of rails 12, 14 may be connected to one another.

The second ends 22, 24 of rails 12, 14 may be connected to one another via a connecting member such as a connecting unit 32, so that a desired distance between rails 12, 14 may be maintained. Rails 12, 14 may extend parallel to one another. For example, the rail 12 and the rail 14 may be connected to one another (e.g., exclusively connected to one another) via the first connecting unit 30 and/or the second connecting unit 32.

Support assembly 20 may be substantially vertically adjustable, e.g., such that the distance between rails 12, 14 and the floor can be adjusted. For this purpose, support assembly 20 may comprise a hand crank 34 for vertical adjustment, and a hand wheel 36 for securing and stabilizing the pedestal of support assembly 20.

The height of the operating table to which rails 12, 14 may be fastened via fastening units 26, 28 may be adjustable by a servo drive, so that by adjusting support assembly 20 and the operating table accordingly, rails 12, 14 can be aligned horizontally at a suitable height.

Two support members such as patient supporting units 40 to 46 for supporting the patient may be arranged on each of rails 12, 14. FIG. 3 illustrates two of these patient supporting units 40, 42 in a side elevation in which, for purposes of simplification, rails 12, 14 are not shown.

Patient supporting units 40 to 46 may (e.g., each) comprise a support pad 50 on which the patient rests. In addition, patient supporting units 40 to 46 may (e.g., each) have a mounting assembly such as a mounting unit 52 for mounting the respective patient supporting unit 40 to 46 on the respective rail 12, 14, and a height adjustment unit or assembly 54, via which support pad 50 may be connected to mounting unit 52 and via which the distance between support pad 50 and mounting unit 52 can be adjusted. For example, a width of the mounting assembly (e.g., mounting unit 52) and of the height adjustment assembly (e.g., height adjustment unit 54) may be substantially equal to a width of the first or second structural members (e.g., rails 12, 14).

Mounting unit 52 may comprise a U-shaped base 56, the recess 58 of which can accommodate the respective rail 12, 14. At the open end of the U-shaped base, a locking clamp 62, which can be locked by a threaded bolt 60, may be provided. To mount patient supporting unit 40 to 46, mounting unit 52 may be placed on the respective rail 12, 14 with locking clamp 62 open, so that said rail may be held within U-shaped recess 58. Locking clamp 62 may then be closed and fastened by threaded bolt 60, allowing for a secure but relatively simple and quick mounting of patient supporting unit 40 to 46 on rails 12, 14. For example, the first support member (e.g., patient supporting unit 40) and the second support member (e.g., patient supporting unit 42) may each be respectively mounted on the first and second structural members (e.g., rails 12 and 14) via a respective mounting assembly (e.g., mounting unit 52) that may be manually releasable and re-fastenable.

Patient supporting units 40, 42 may serve for example to support the upper body of a patient, whereas patient supporting units 44, 46 may serve for example to support the lower body (e.g., hips) of the patient. The patient may rest with his head toward support assembly 20, and with his legs resting on a part of the patient supporting surface of the actual operating table 100. To support the head, additional patient supporting units may be for example mounted on rails 12, 14.

Patient supporting units 40, 44 may be mounted (e.g., exclusively mounted) on the first rail 12, and patient supporting units 42, 46 may be mounted (e.g., exclusively mounted) on the second rail 14. There may be no connection between patient supporting units 40 and 42 and between 44 and 46, which may be situated side by side.

Patient supporting units 40 to 46 may be displaced individually (e.g., independently of one another) along rails 12, 14, so that for example, when combined with the vertical adjustment of patient supporting units 40 to 46, a suitable adjustment to the individual anatomy of a patient to undergo surgery may be provided. Also for example, patient supporting units 40 to 46 may not be arranged directly side by side. Further for example, support pads 50 may also be arranged at different heights. The distance between support pads 50 of adjacent patient supporting units 40 and 42 or 44 and 46 may also be varied since the support pads may be mounted on height adjustment unit 54 (e.g., so as to be transversely displaceable).

As illustrated in FIGS. 2 and 3, the distance between rails 12 and 14 and the dimensions of patient supporting units 40 to 46 may be selected such that an open space may be formed between the mutually facing sides of support pads 50 mounted on different rails 12, 14. This distance between support pads 50 (e.g., and the lack of an interconnection of patient supporting units 40, 42 and 44, 46 arranged side by side) may result in the formation of a material-free x-ray area (e.g., as indicated by a rectangle and identified by reference sign 70 in the exemplary configuration illustrated in FIG. 2). In this material-free x-ray area 70, the x-rays may not be impacted by substantially any material, so that a suitable x-ray image, for example of the spinal column (which may be located in this area if the patient is suitably supported) is provided. For example, a first support member (e.g., patient support unit 40) and a second support member (e.g., patient support member 42) may be spaced apart from one another (e.g., with a spacing 70 disposed between them).

Support pads 50 of patient supporting units 40 to 46 may be made of a radiolucent material, for example, a carbon fiber-reinforced plastic. Furthermore, the shape thereof may be designed to be relatively homogeneous and thin in an area adjoining the x-ray area, in order to substantially prevent differences in x-ray absorption that would be reflected in an x-ray image. Thus support pads 50, for example in those areas in which they project toward x-ray area 50 from mounting unit 52 and height adjustment unit 54, may be highly radiolucent, resulting in a supplemental x-ray area 72 (e.g., as indicated in FIG. 3, in which an x-ray image of suitable quality is provided). When combined with x-ray area 70, an expanded x-ray area 74 may be provided, which can be used during the surgical operation. For example, the first support member (e.g., patient supporting unit 40) may include a first overhanging portion (e.g., portion of support pad 50 overhanging at reference numeral 72) made of radiolucent material and the second support member (e.g., patient supporting unit 42) may include a second overhanging portion (e.g., portion of support pad 50 overhanging at reference numeral 72) made of radiolucent material. Also for example, the first overhanging portion (e.g., portion of support pad 50 overhanging at reference numeral 72 of patient supporting unit 40) may be disposed opposite to the second overhanging portion (e.g., portion of support pad 50 overhanging at reference numeral 72 of patient supporting unit 42). For example, as illustrated in FIGS. 2 and 3, the first and second overhanging portions may be disposed opposite from each other, as separated for example by a distance such as reference numeral 70. Patient supporting units 44 and 46 may respectively include similar overhanging portions.

Mounting unit 52 and height adjustment unit 54 may be configured to project relatively little above rails 12, 14 in the direction of x-ray area 70, so that a relatively large supplemental x-ray area 72 may be formed (e.g., making expanded x-ray area 74 relatively large).

Apparatus 10 described above may provide suitable flexibility in adjustment to the individual anatomy of a patient, and may also enable x-ray images of suitable quality to be recorded.

It will be apparent to those skilled in the art that various modifications and variations can be made to the disclosed method and apparatus. Other embodiments will be apparent to those skilled in the art from consideration of the specification and practice of the disclosed method and apparatus. It is intended that the specification and the disclosed examples be considered as exemplary only, with a true scope being indicated by the following claims.

What is claimed is:

1. An apparatus for supporting a patient, comprising:
a first structural member having a first end portion and a second end portion, the second end portion of the first structural member being attached to an operating table;
a second structural member having a first end portion and a second end portion, the second end portion of the second structural member being attached to the operating table;
a first connecting member that connects the first end of the first structural member to the first end of the second structural member, the first structural member being disposed at a predetermined distance from the second structural member;
a first support member supported exclusively on the first structural member, the first support member configured to support a body part of the patient; and
a second support member supported exclusively on the second structural member;
wherein the first support member comprises a mounting assembly and is configured to be reversibly locked onto the first structural member, and when not locked is displaceable along the first structural member along a lengthwise direction of the first structural member;
wherein the second support member comprises a mounting assembly and is configured to be reversibly locked onto the second structural member, and when not locked is displaceable along the second structural member along a lengthwise direction of the second structural member independent of the positioning of the first support member on the first structural member;
wherein the first support member comprises a first support pad and a first height adjustment assembly for varying the height of the first support pad with respect to the first structural member when the first support member is mounted to the first structural member;
wherein the second support member comprises a second support pad and a second height adjustment assembly for varying the height of the second support pad with respect to the second structural member when the second support member is mounted to the second structural member;
wherein the first support member and the second support member are spaced apart from one another, a material-free x-ray area being formed between the first support member and the second support member.

2. The apparatus according to claim 1, wherein there is no connection between the first support member and the second support member.

3. The apparatus according to claim 1, wherein the second end portion of the first structural member and the second end portion of the second structural member are connected to one another via a second connecting member.

4. The apparatus according to claim 1, wherein the first structural member and the second structural member are connected to one another exclusively via the first connecting member.

5. The apparatus according to claim 1, wherein:
the mounting assembly of the first support member and the second support member each comprises a U-shaped base; and
a locking clamp is pivotably disposed at the U-shaped base, the locking clamp tightenable via a threaded fastener.

6. The apparatus according to claim 1, wherein the first connecting member is supported by a height-adjustable support assembly.

7. The apparatus according to claim 1, wherein a first fastening assembly that fastens the apparatus to the operating table is disposed at the second end portion of the first structural member, and a second fastening assembly that fastens the apparatus to the operating table is disposed at the second end portion of the second structural member.

8. The apparatus according to claim 1, wherein a third support member is disposed on the first structural member and a fourth support member is disposed on the second structural member.

9. The apparatus according to claim 1, wherein an upper pad surface of the first support pad is configured to be parallel to or coplanar with an upper pad surface of the second support pad.

10. The apparatus according to claim 1, wherein the respective mounting assembly of each of the first support member and the second support member is manually releasable and re-fastenable.

11. An apparatus for supporting a patient, comprising:
a first structural member having a first end portion and a second end portion, the second end portion of the first structural member being attached to an operating table;
a second structural member having a first end portion and a second end portion, the second end portion of the second structural member being attached to the operating table;
a first connecting member that connects the first end of the first structural member to the first end of the second structural member, the first structural member being disposed at a predetermined distance from the second structural member;
a first support member supported on the first structural member and not the second structural member and also configured to establish a locked state and an unlocked state with respect to the first structural member, and when in the unlocked state the first support member is permitted to be located at various locations along the first structural member, the first support member configured to support a body part of the patient; and
a second support member supported on the second structural member and not the first structural member and also configured to establish a locked state and an unlocked state with respect to the second structural member, and when in the unlocked state the second support member is permitted to be located at various locations along the second structural member irrespective of the location of the first support member's location with respect to the first structural member;
wherein the first support member comprises a first pad surface and the second support member comprises a second pad surface, at least one of the first support member and the second support member comprising a height adjustment assembly that is configured to permit the vertical displacement of the first pad surface with respect to the second pad surface;

wherein the first support member and the second support member are spaced apart from one another, a material-free x-ray area being formed between the first support member and the second support member;

wherein the first support member includes a first overhanging portion and the second support member includes a second overhanging portion; and wherein the first overhanging portion and second overhanging portion are made of a radiolucent material.

12. The apparatus according to claim 11, wherein the first overhanging portion is disposed opposite to the second overhanging portion.

13. The apparatus according to claim 12, wherein the first overhanging portion has a homogeneous thickness and the second overhanging portion has a homogeneous thickness.

14. The apparatus according to claim 12, wherein the first overhanging portion is a portion of a support pad of the first support member and the second overhanging portion is a portion of a support pad of the second support member.

15. An apparatus for supporting a patient, comprising:
a first structural member having a first end portion and a second end portion, the second end portion of the first structural member being attached to an operating table;
a second structural member having a first end portion and a second end portion, the second end portion of the second structural member being attached to the operating table;
a first connecting member that connects the first end of the first structural member to the first end of the second structural member, the first structural member being disposed at a predetermined distance from the second structural member;
a first support member supported on the first structural member and not the second structural member, the first support member configured to support a body part of the patient; and
a second support member supported on the second structural member and not the first structural member;
wherein the first support member and the second support member are spaced apart from one another, a material-free x-ray area being formed between the first support member and the second support member;
wherein the first support member includes a first overhanging portion and the second support member includes a second overhanging portion;
wherein the first overhanging portion and second overhanging portion are made of a radiolucent material; and
wherein the each of the first support member and the second support member includes a mounting assembly, a support pad for supporting the patient, and a height adjustment assembly, which is disposed between the mounting assembly and the support pad, and wherein a distance between the support pad and the mounting assembly for each of the first support member and the second support member is adjustable via the height adjustment assembly.

16. The apparatus according to claim 15, wherein a width of the mounting assembly and of the height adjustment assembly is substantially equal to a width of the first or second structural members.

17. An apparatus for supporting a patient, comprising:
a first rail having a first end portion and a second end portion, the second end portion of the first rail being attached to an operating table;
a second rail having a first end portion and a second end portion, the second end portion of the second rail being attached to the operating table;
a first connecting member that connects the first end of the first rail to the first end of the second rail, the first rail being disposed at a predetermined distance from the second rail;
a first support member disposed on the first rail, the first support member configured to support a body part of the patient; and
a second support member disposed on the second rail;
wherein the first support member is supported exclusively by the first rail and the second support member is supported exclusively by the second rail;
wherein each of the first support member and the second support member comprises a support pad;
wherein the first support member can be secured to the first rail by a first support member mounting unit and the second support member can be secured to the second rail by a second support member mounting unit, and while secured to their respective rails, both (i) the support pad of the first support member can be elevated with respect to the first support member mounting unit by a height adjustment unit of the first support member, and (ii) the support pad of the second support member can be elevated with respect to the second support member mounting unit by a height adjustment unit of the second support member; and
wherein the first support member and the second support member are spaced apart from one another, a material-free x-ray area being formed between the first support member and the second support member.

18. The apparatus according to claim 17, wherein a third support member is disposed exclusively on the first rail and a fourth support member is disposed exclusively on the second rail.

19. The apparatus according to claim 18, wherein the first support member and the second support member support an upper body of the patient and the third support member and the fourth support member support a lower body of the patient.

20. The apparatus according to claim 17, wherein at least one of the first rail, the second rail, the first support member, and the second support member are made from a carbon fiber-reinforced plastic material.

* * * * *